United States Patent [19]

Martinelli

[11] Patent Number: 5,779,122

[45] Date of Patent: Jul. 14, 1998

[54] ASTHMA MEDICATION POUCH

[76] Inventor: Vincent Martinelli, 255-29 75 Ave., Glen Oaks, N.Y. 11004

[21] Appl. No.: 851,210

[22] Filed: May 5, 1997

[51] Int. Cl.⁶ ............................................. A45F 5/00
[52] U.S. Cl. .................... 224/683; 224/666; 224/222; 224/680; 224/236; 224/240
[58] Field of Search ............................ 224/153, 191, 224/627–630, 645, 650–655, 219, 222, 676, 677, 678, 680–684, 235, 236, 240, 250, 660, 665–669, 673, 908; D3/215, 224, 225, 226, 230; 150/112, 113, 114, 117; 190/102, 111, 127

[56] References Cited

U.S. PATENT DOCUMENTS

| | | | |
|---|---|---|---|
| D. 288,865 | 3/1987 | Nace | D3/106 |
| D. 359,616 | 6/1995 | Ishibashi | D3/218 |
| D. 362,540 | 9/1995 | McNamara et al. | D3/226 |
| 367,996 | 8/1887 | Nathan | 224/683 |
| 3,300,109 | 1/1967 | Clark | 224/667 |
| 4,330,073 | 5/1982 | Clark | 224/223 |
| 4,588,056 | 5/1986 | Bernbaum | 190/127 |
| 4,993,614 | 2/1991 | Bonofiglo | 224/665 |
| 5,172,838 | 12/1992 | Rowell et al. | 224/680 |
| 5,205,448 | 4/1993 | Kester et al. | 224/908 |
| 5,350,046 | 9/1994 | Falloon et al. | 190/127 |
| 5,370,288 | 12/1994 | Field | 224/223 |
| 5,443,192 | 8/1995 | Hodges et al. | |

*Primary Examiner*—Allan N. Shoap
*Assistant Examiner*—Gregory M. Vidovich
*Attorney, Agent, or Firm*—Richard L. Miller, P.E

[57] ABSTRACT

An asthma medication pouch that is adaptable to be replaceably attachable to one of a belt, clothing, and an ankle of an asthma patient, and carries asthma medications for the asthma patient. The asthma medication pouch includes a primary pouch for carrying at least one spray inhaler for the asthma patient, an elastic band that is disposed on the primary pouch for carrying an intramuscular injection of adrenaline for the asthma patient, attaching apparatus for attaching the asthma medication pouch to one of the belt, the clothing, and the ankle, and a secondary pouch that is disposed on the primary pouch for carrying asthma pills for the asthma patient.

22 Claims, 2 Drawing Sheets

ASTHMA MEDICATION POUCH

BACKGROUND OF THE INVENTION

1. Field of the Invention

The present invention relates to a pouch. More particularly, the present invention relates to an asthma medication pouch.

2. Description of the Prior Art

When avid runners and cyclists who have asthma compete in races, they must always have their spray inhalers and medication ready for instant use to help restore breathing and provide relief during an asthma attack. People with asthma attest to its uncomfortable, painful, and debilitating symptoms. Asthma is one of the top five causes of death in the United States.

While working or running, the inhaler is kept in a sock or stuck in a waistband. This causes it to get dusty and sweaty, and therefore rendering it ineffective when sprayed in the mouth. Keeping the inhaler in the pocket is cumbersome at best.

Numerous innovations for belt pouches have been provided in the prior art that will be described. Even though these innovations may be suitable for the specific individual purposes to which they address, however, they differ from the present invention.

FOR EXAMPLE, U.S. Pat. No. Des. 288,865 to Nace teaches the ornamental design for a belt mounted telephone cradle.

ANOTHER EXAMPLE, U.S. Pat. No. Des. 359,616 to Ishibashi et al. teaches the ornamental design for a beeper holder.

FINALLY, STILL ANOTHER EXAMPLE, U.S. Pat. No. 5,443,192 to Hodges et al. teaches a holster apparatus for use in combination with a self-protection chemical dispenser having a cylindrical body equipped with a spray nozzle and an actuator button. The holster includes a casing having a body portion for receiving the dispenser. The casing also includes a first retainer at one end thereof which can be a flap and a second retainer at the other end thereof for selectively holding the dispenser in the casing in the position so that the dispenser can be actuated by the actuator button to cause protective chemicals to be sprayed from the spray nozzle while the dispenser is in the casing. Separate belt connectors adapted to be attached to a user's belt and an attaching structure is provided for operably connecting or disconnecting the casing to the belt connector whereby the casing with the dispenser therein can be quickly and easily accessed for use or stored away for immediate re-access. A structure is provided for allowing the device to quickly convert from left hand to right hand use on an officer's belt. Structure is provided for making it difficult to open the flap on the casing and another structure is provided for making it difficult for an unauthorized person to remove the dispenser from the casing.

It is apparent that numerous innovations for belt pouches have been provided in the prior art that are adapted to be used. Furthermore, even though these innovations may be suitable for the specific individual purposes to which they address, however, they would not be suitable for the purposes of the present invention as heretofore described.

SUMMARY OF THE INVENTION

ACCORDINGLY, AN OBJECT of the present invention is to provide an asthma medication pouch that avoids the disadvantages of the prior art.

ANOTHER OBJECT of the present invention is to provide an asthma medication pouch that is simple and inexpensive to manufacture.

STILL ANOTHER OBJECT of the present invention is to provide an asthma medication pouch that is simple to use.

BRIEFLY STATED, YET ANOTHER OBJECT of the present invention is to provide an asthma medication pouch that is adaptable to be replaceably attachable to one of a belt, clothing, and an ankle of an asthma patient, and carries asthma medications for the asthma patient. The asthma medication pouch includes a primary pouch for carrying at least one spray inhaler for the asthma patient, an elastic band that is disposed on the primary pouch for carrying an intramuscular injection of adrenaline for the asthma patient, attaching apparatus for attaching the asthma medication pouch to one of the belt, the clothing, and the ankle, and a secondary pouch that is disposed on the primary pouch for carrying asthma pills for the asthma patient.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

DESCRIPTION OF THE DRAWING

The figures on the drawing are briefly described as follows.

Figure 1:
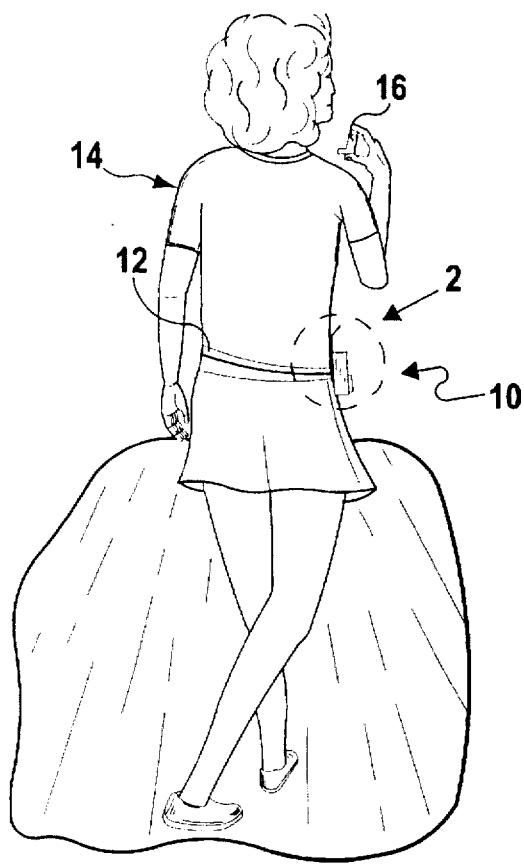
FIG. 1 is a diagrammatic perspective view of the present invention being utilized by an asthma patient.

LIST OF REFERENCE NUMERALS UTILIZED IN THE DRAWING 10 asthma medication pouch of the present invention
12 waist belt of asthma patient 14
14 asthma patient
16 inhaler
18 primary pouch
20 back wall of primary pouch 18
22 top edge of back wall 20 of primary pouch 18
23 inner surface of back wall 20 of primary pouch 18
24 pair of side walls of primary pouch 18
26 front wall of primary pouch 18
28 top edge of front wall 26 of primary pouch 18
29 loop portion on top edge 28 of front wall 26 of primary pouch 18
30 bottom wall of primary pouch 18
31 receptacle in primary pouch 18
33 top of primary pouch 18
35 sub-receptacles of receptacle 31 in primary pouch 18
37 at least one partition in receptacle 31 in primary pouch 18
32 flap of primary pouch 18
34 free end of flap 32 of primary pouch 18
36 inner surface of free end of flap 32 of primary pouch 18

38 hook portion on inner surface 36 of free end of flap 32 of primary pouch 18
40 elastic band
42 card
44 rivets
46 spring clip
48 one leg of spring clip 46
50 another leg of spring clip 46
52 pair of slots in another leg of spring clip 46
54 strap
56 pocket
58 I.D. tag
60 secondary pouch
62 back wall of secondary pouch 60
64 pair of side walls of secondary pouch 60
66 front wall of secondary pouch 60
68 top edge of front wall 66 of secondary pouch 60
70 loop portion
72 bottom wall of secondary pouch 60
74 receptacle in secondary pouch 60
76 top of secondary pouch 60
78 flap of secondary pouch 60
80 free end of flap 78 of secondary pouch 60
82 inner surface of free end 80 of flap 78 of secondary pouch 60
84 hook portion
86 vital asthma pills
88 intramuscular injection of adrenaline

DESCRIPTION OF THE PREFERRED EMBODIMENT

Referring now to the figures in which like numerals indicate like parts, and particularly to FIG. 1, the asthma medication pouch of the present invention is shown generally at 10 replaceably carried on a waist belt 12 of an asthma patient 14 who is utilizing an inhaler 16 stored in the asthma medication pouch 10.

It is to be understood, however, that the asthma medication pouch 10 being carried on the waist belt 12 of the asthma patient 14 is for illustrative purposes, and that it can be carried on any other type of belt, such as, but limited to, clothing, belt band, and a belt around the ankle without departing in any way from the spirit of the present invention.

Figure 2:
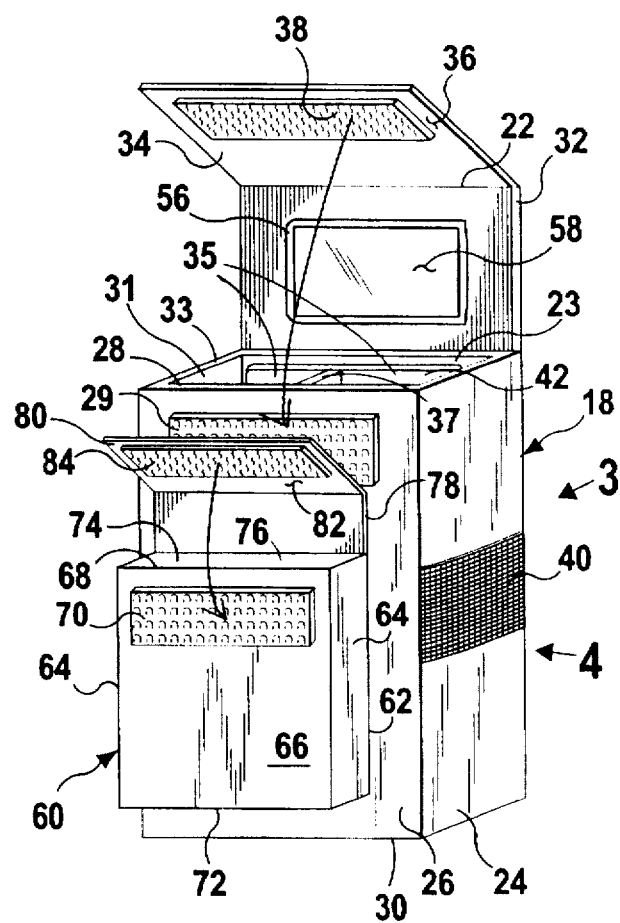
FIG. 2 is a diagrammatic front perspective view of the area generally enclosed by the dotted circle identified by arrow 2 in FIG. 1 and illustrating the present invention.
Figure 3:
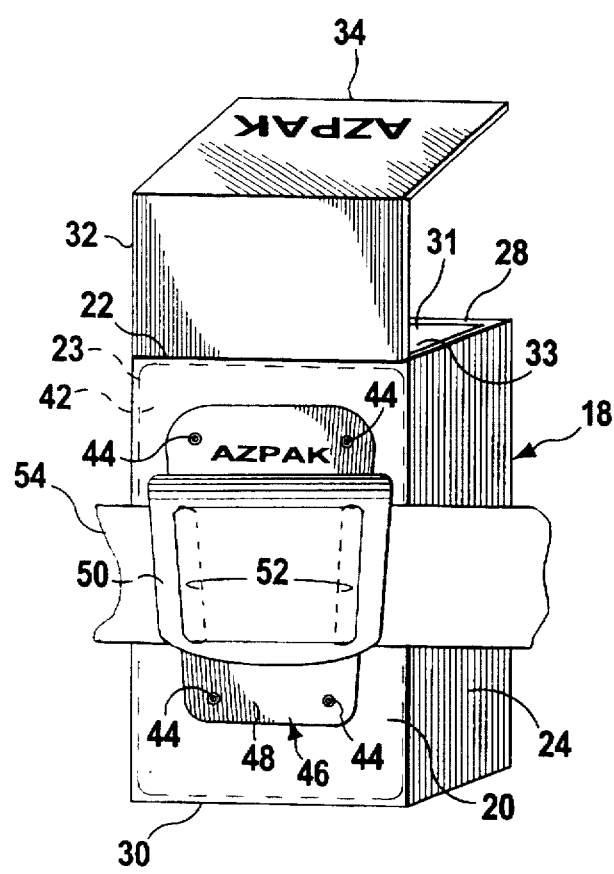
FIG. 3 is a diagrammatic back perspective view of the present invention taken generally in the direction of arrow 3 in FIG. 2.

The configuration of the asthma medication pouch 10 can best be seen in FIGS. 2 and 3, and as such will be discussed with reference thereto.

The asthma medication pouch 10 includes a primary pouch 18 that is hollow, rectangular-parallelepiped-shaped, and double-walled nylon with insulation therebetween sold under the tradename GORTEX(TM).

The primary pouch 18 has a back wall 20 that is closed and rectangular-shaped and has a top edge 22 and an inner surface 23.

The primary pouch 18 further has a pair of side walls 24 that are closed and rectangular-shaped.

The primary pouch 18 further has a front wall 26 that is closed and rectangular-shaped and has a top edge 28 with a loop portion 29 of hook and loop fasteners sewn transversely thereacross on its outer surface.

The primary pouch 18 further has a bottom wall 30 that is closed and rectangular-shaped.

The back wall 20 of the primary pouch 18, the pair of side walls 24 of the primary pouch 18, the front wall 26 of the primary pouch 18, and the bottom wall 30 of the primary pouch 18 together define therebetween a receptacle 31 which can be divided into a plurality of sub-receptacles 35 by at least one partition 37 that is rectangular-shaped and divides the receptacle 31 in the primary pouch 18 longitudinally.

The primary pouch 18 further has a top 33 that is open and communicates with the receptacle 31 in the primary pouch 18.

The primary pouch 18 further has a flap 32 that is rectangular-shaped and integrally-formed with, and extends upwardly and forwardly from, the top edge 22 of the back wall 20 of the primary pouch 18.

The flap 32 of the primary pouch 18 has a free end 34 with an inner surface 36 that has a hook portion 38 of the hook and loop fasteners sewn transversely thereacross that mates with the loop portion 29 of the hook and loop fasteners on the front 26 of the primary pouch 18 to selectively open and close the open top 33 of the primary pouch 18. asthma medication pouch 10 further includes an elastic band 40 that is slender and extends transversely across one side wall 24 of the pair of side walls 24 at a midway point thereof, and is sewn thereto at the its ends.

The asthma medication pouch 10 further includes a card 42 that is hard plastic and affixed to the inner surface 23 of the back wall 20 of the primary pouch 18 by rivets 44 and adds rigidity thereto.

The asthma medication pouch 10 further includes a spring clip 46 for attaching the asthma medication pouch 10 to a belt or waist band of pants from above.

The spring clip 46 is plastic, generally inverted U-shaped, and has one leg 48 thereof affixed to the back wall 20 of the primary pouch 18 by the rivets 44, with the back wall 20 of the primary pouch 18 disposed between, and abutting against, the one leg 48 of the clip 46 and the card 42.

The spring clip 46 has another leg 50 with a pair of slots 52 that are slender and extend vertically therein and receive a strap 54 that is nylon and has hook and loop fasteners thereon for affixing the asthma medication pouch 10 around an ankle of the asthma patient 14.

The asthma medication pouch 10 further includes a pocket 56 that is transparent and is sewn to the flap 32 of the primary pouch 18 at its inside surface and has replaceably slidable therein an I.D. tag 58 with pedigree and medical instructions thereon in case of emergency.

The asthma medication pouch 10 includes a secondary pouch 60 that is hollow, rectangular-parallelepiped-shaped, and double-walled nylon with insulation therebetween sold under the tradename GORTEX(TM).

The secondary pouch 60 has a back wall 62 that is closed, rectangular-shaped, is affixed directly against the front wall 26 of the primary pouch 18 at its outer surface, and is disposed between the top edge 28 of the front wall 26 of the primary pouch 18 and the bottom wall 30 of the primary pouch 18.

The secondary pouch 60 further has a pair of side walls 64 that are closed and rectangular-shaped.

The secondary pouch 60 further has a front wall 66 that is closed and rectangular-shaped and has a top edge 68 with a loop portion 70 of hook and loop fasteners sewn transversely thereacross on its outer surface.

The secondary pouch 60 further has a bottom wall 72 that is closed and rectangular-shaped.

The back wall 62 of the secondary pouch 60, the pair of side walls 64 of the secondary pouch 60, the front wall 66 of the secondary pouch 60, and the bottom wall 72 of the secondary pouch 60 define therebetween a receptacle 74.

The secondary pouch 60 further has a top 76 that is open and communicates with the receptacle 74 in the secondary pouch 60.

The secondary pouch 60 further has a flap 78 that is rectangular-shaped and integrally-formed with, and extends upwardly and forwardly from, the back wall 62 of the secondary pouch 60 at its top edge.

The flap 78 has a free end 80 with an inner surface 82 that has a hook portion 84 of the hook and loop fasteners sewn transversely thereacross that mates with the loop portion 70 of the hook and loop fasteners on the front wall 66 of the secondary pouch 60 to selectively open and close the open top 74 of the secondary pouch 60.

Figure 4:
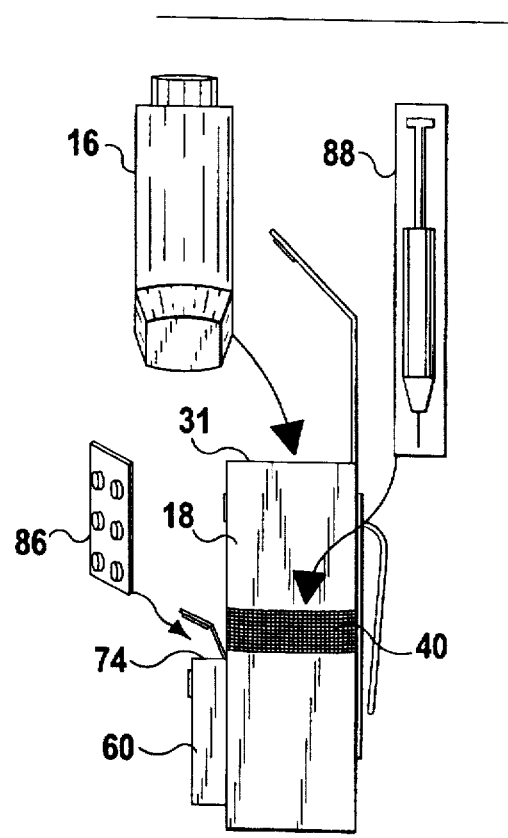
FIG. 4 is a diagrammatic side elevational view of the present invention, illustrating the positioning of the various asthma medication therein.

The positioning of the asthma medications in the asthma medication pouch 10 can best be seen in FIG. 4, and as such will be discussed with reference thereto.

The receptacle 74 in the secondary pouch 60 houses vital asthma pills 86, such as, but not limited to, theopy-line, prednisone, and albuterol.

The band 40 houses an intramuscular injection of adrenaline 88 sold under the tradename EPI-PEN(TM).

The receptacle 31 in the primary pouch 18 houses at least one of the spray inhaler 16 and a cortico-steroid inhaler sold under the tradename ASMA-CRT(TM).

It will be understood that each of the elements described above, or two or more together, may also find a useful application in other types of constructions differing from the types described above.

While the invention has been illustrated and described as embodied in an asthma medication pouch, however, it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An asthma medication pouch adaptable to be replaceably attachable to one of a belt, clothing, and an ankle of an asthma patient, and carrying asthma medications for the asthma patient, comprising:
  a) a primary pouch for carrying at least one spray inhaler for the asthma patient; said primary pouch having a back wall being closed and rectangular-shaped and having a top edge and an inner surface;
  b) an elastic band disposed on said primary pouch for carrying an intramuscular injection of adrenaline for the asthma patient;
  c) attaching means for attaching said asthma medication pouch to one of the belt, the clothing, and the ankle;
  d) a secondary pouch disposed on said primary pouch for carrying asthma pills for the asthma patient;
  e) a card being hard plastic and affixed to said inner surface of said back wall of said primary pouch, by rivets so as to add rigidity thereto; said attaching means including a spring clip being plastic, generally inverted U-shaped, and having one leg thereof affixed to said back wall of said primary pouch by said rivets, with said back wall of said primary pouch disposed between, and abutting against, said one leg of said clip of said attaching means and said card.

2. The asthma medication pouch as defined in claim 1, wherein said primary pouch is hollow, rectangular-parallelepiped-shaped, and double-walled nylon with insulation therebetween.

3. The asthma medication pouch as defined in claim 1, wherein said primary pouch further has a pair of side walls that are closed and rectangular-shaped.

4. The asthma medication pouch as defined in claim 3, wherein said primary pouch further has a front wall that is closed and rectangular-shaped and has a top edge with a loop portion of hook and loop fasteners sewn transversely thereacross on its outer surface.

5. The asthma medication pouch as defined in claim 4, wherein said primary pouch further has a bottom wall that is closed and rectangular-shaped.

6. The asthma medication pouch as defined in claim 5, wherein said back wall of said primary pouch, said pair of side walls of said primary pouch, said front wall of said primary pouch, and said bottom wall of said primary pouch together define therebetween a receptacle for carrying the at least one spray inhaler for the asthma patient.

7. The asthma medication pouch as defined in claim 6, wherein said receptacle in said primary pouch is divided into a plurality of sub-receptacles by at least one partition that is rectangular-shaped and divides said receptacle in said primary pouch longitudinally.

8. The asthma medication pouch as defined in claim 6, wherein said primary pouch further has a top that is open and communicates with said receptacle in said primary pouch.

9. The asthma medication pouch as defined in claim 8, wherein said primary pouch further has a flap that is rectangular-shaped and integrally-formed with, and extends upwardly and forwardly from, said top edge of said back wall of said primary pouch.

10. The asthma medication pouch as defined in claim 9, wherein said flap of said primary pouch has a free end with an inner surface that has a hook portion of said hook and loop fasteners sewn transversely thereacross that mates with said loop portion of said hook and loop fasteners on said front wall of said primary pouch to selectively open and close said open top of said primary pouch.

11. The asthma medication pouch as defined in claim 3, wherein said elastic band is slender and extends transversely across one side wall of said pair of side walls of said primary pouch, at a midway point thereof, and is sewn thereto at its ends.

12. The asthma medication pouch as defined in claim 1, wherein said spring clip of said attaching means has another leg with a pair of slots that are slender and extend vertically therein and receive a strap that is nylon and has hook and loop fasteners thereon for affixing said asthma medication pouch around the ankle of the asthma patient.

13. The asthma medication pouch as defined in claim 9, further comprising a pocket that is transparent and is sewn to said flap of said primary pouch at its inside surface, and has replaceably slidable therein, an I.D. tag with pedigree and medical instructions thereon of the asthma patient in case of emergency.

14. The asthma medication pouch as defined in claim 1, wherein said secondary pouch is hollow, rectangular-parallelepiped-shaped, and double-walled nylon with insulation therebetween.

15. The asthma medication pouch as defined in claim 5, wherein said secondary pouch has a back wall that is closed, rectangular-shaped, is affixed directly against said outer surface of said front wall of said primary pouch, and is disposed between said top edge of said front wall of said primary pouch and said bottom wall of said primary pouch.

16. The asthma medication pouch as defined in claim 15, wherein said secondary pouch further has a pair of side walls that are closed and rectangular-shaped.

17. The asthma medication pouch as defined in claim 16, wherein said secondary pouch further has a front wall that is closed and rectangular-shaped and has a top edge with a loop portion of hook and loop fasteners sewn transversely thereacross on its outer surface.

18. The asthma medication pouch as defined in claim 17, wherein said secondary pouch further has a bottom wall that is closed and rectangular-shaped.

19. The asthma medication pouch as defined in claim 18, wherein said back wall of said secondary pouch, said pair of side walls of said secondary pouch, said front wall of said secondary pouch, and said bottom wall of said secondary pouch define therebetween a receptacle for storing the asthma pills for the asthma patient.

20. The asthma medication pouch as defined in claim 19, wherein said secondary pouch further has a top that is open and communicates with said receptacle in said secondary pouch.

21. The asthma medication pouch as defined in claim 20, wherein said secondary pouch further has a flap that is rectangular-shaped and integrally-formed with, and extends upwardly and forwardly from, said back wall of said secondary pouch, at its top edge.

22. The asthma medication pouch as defined in claim 21, wherein said flap of said secondary pouch has a free end with an inner surface that has a hook portion of said hook and loop fasteners sewn transversely thereacross that mates with said loop portion of said hook and loop fasteners on said front wall of said secondary pouch to selectively open and close said open top of said secondary pouch.

* * * * *